(12) United States Patent
Kinnett

(10) Patent No.: US 6,852,115 B2
(45) Date of Patent: Feb. 8, 2005

(54) MULTI-FUNCTIONAL ORTHOPEDIC SURGICAL INSTRUMENT AND METHOD OF USING SAME

(75) Inventor: J. Gregory Kinnett, 5534 St. Charles Ave., New Orleans, LA (US) 70115

(73) Assignee: J. Gregory Kinnett, New Orleans, LA (US)

( * ) Notice: Subject to any disclaimer, the term of this patent is extended or adjusted under 35 U.S.C. 154(b) by 0 days.

(21) Appl. No.: 10/600,956

(22) Filed: Jun. 20, 2003

(65) Prior Publication Data

US 2004/0087960 A1 May 6, 2004

Related U.S. Application Data

(62) Division of application No. 09/747,047, filed on Dec. 21, 2000, now Pat. No. 6,613,052.

(51) Int. Cl.[7] ............................................. A61B 17/15
(52) U.S. Cl. ........................................ 606/88; 606/89
(58) Field of Search ........................ 606/86–88, 62–64

(56) References Cited

U.S. PATENT DOCUMENTS

| | | | |
|---|---|---|---|
| 3,779,239 A | 12/1973 | Fischer et al. | |
| 4,453,539 A | 6/1984 | Raftopoulos et al. | |
| 4,457,307 A | 7/1984 | Stillwell | |
| 4,492,226 A | 1/1985 | Belykh et al. | |
| 4,520,511 A | 6/1985 | Gianezio et al. | |
| 5,275,603 A | * 1/1994 | Ferrante et al. | 606/86 |
| 5,342,367 A | * 8/1994 | Ferrante et al. | 606/86 |
| 5,486,178 A | 1/1996 | Hodge | |
| 5,601,563 A | * 2/1997 | Burke et al. | 606/86 |
| 5,649,928 A | 7/1997 | Grundei | |
| 5,674,223 A | 10/1997 | Cipolletti | |
| 5,735,904 A | 4/1998 | Pappas | |
| 5,741,264 A | 4/1998 | Cipoletti | |
| 5,749,876 A | 5/1998 | Duvillier et al. | |
| 5,925,049 A | 7/1999 | Gustilo et al. | |

* cited by examiner

Primary Examiner—David O. Reip
Assistant Examiner—D. Jacob Davis
(74) Attorney, Agent, or Firm—Jenkens & Gilchrist, P.C.

(57) ABSTRACT

An apparatus has been developed to enable a surgeon to perform multiple orthopedic surgical operations, such as orthopedic surgical resectioning, total joint replacement and fixation of fractures, based on a single reference point. The apparatus is adjustable to conform to the needs and dimensions of individual patients and the surgical procedure(s) to be performed. The apparatus includes a support adapted for insertion into and alignment within the medullary cavity of a patient's bone. The support is capable of expanding into the bone so that the support is fixed within the bone and alignable to the bone. The support may be implanted to align a fractured bone, or extend a distance beyond its fixed position within the medullary cavity to provide a known surgical reference point. The apparatus includes one or more cutting guides mountable on the support and used in performing the desired surgical procedure(s). The cutting guides are positionable with respect to the known surgical reference point created by the support which enables the user to accurately position and secure various instruments at the desired position about the patient's anatomy.

21 Claims, 11 Drawing Sheets

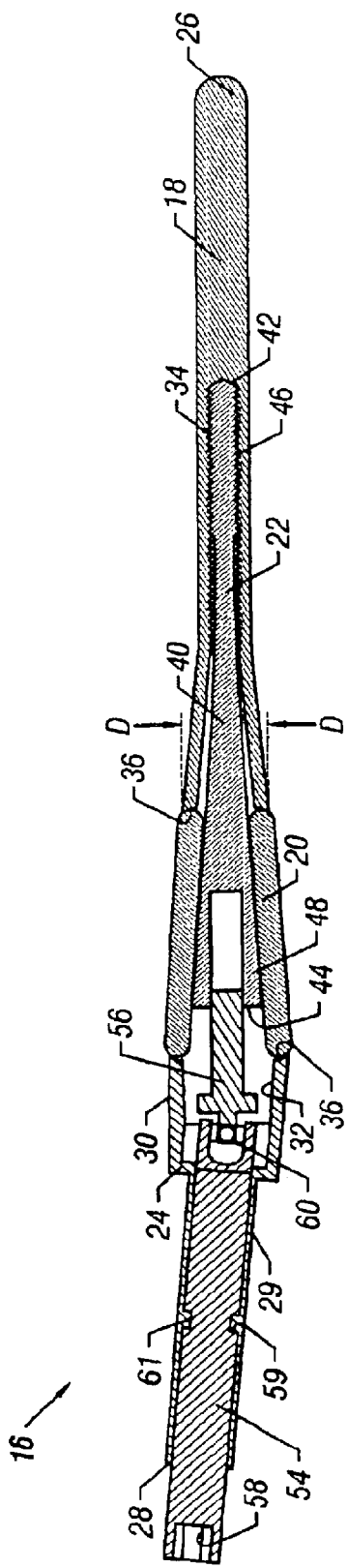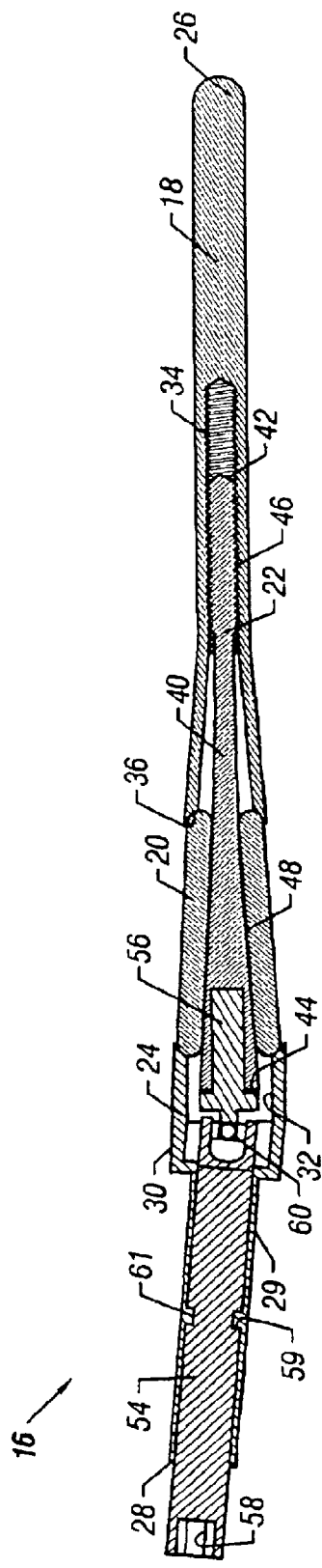
FIG. 4
FIG. 5

MULTI-FUNCTIONAL ORTHOPEDIC SURGICAL INSTRUMENT AND METHOD OF USING SAME

CROSS-REFERENCE TO PRIOR APPLICATIONS

This is a divisional application claiming benefit of U.S. application Ser. No. 09/747,047, filed Dec. 21, 2000 now U.S. Pat. No. 6,613,052, which is incorporated by reference herein in its entirety.

FEDERALLY SPONSORED RESEARCH STATEMENT

Not applicable.

REFERENCE TO AN APPENDIX

Not applicable.

FIELD OF THE INVENTION

The invention relates to a multi-functional surgical instrument for performing orthopedic surgical resectioning, total joint replacement and fixation of fractures. The invention also relates to a method of resectioning the femur and/or tibia bones in preparation for implantation of a knee prosthesis.

BACKGROUND OF THE INVENTION

Surgical manipulation of joints and bones requires efficient and accurate instruments adaptable to an individual patient. Such surgeries directly affect the alignment of the patient's bones and the function of related joints which, in turn, impact the patient's pain, range of motion, ambulation and more. Surgical instruments have been developed to assist surgeons in performing orthopedic surgeries, such as the reconstruction of fractured bones, the preparation of bones and the implantation of total joint prostheses. These surgeries involve delicate procedures that are necessary to enable patients to move properly and without pain. The accuracy of surgical cuts to the patient's bones is important in assuring proper bone alignment and the best possible fit and alignment of any implanted prostheses. Moreover, it is important to the success of the operation that the number of surgical manipulations be reduced to shorten surgical time, prevent blood loss or infection, reduce anesthesia and eliminate further violation or manipulation of soft tissue or bone.

A typical orthopedic surgical instrument used for resectioning joint surfaces during knee surgery involves mounting a cutting fixture to a patient's femur to determine where to make cuts to the femur and/or adjacent tibia. These devices provide surgical references used for cutting the distal end of a femur and/or the proximal end of an adjacent tibia to create a surface to implant a knee prosthesis. However, these instruments typically have limited adaptability to the patient's anatomy and require significant skill by multiple individuals to perform the proper cuts. Furthermore, such instruments also involve complex parts difficult for one person to manipulate, particularly under time restricted surgical conditions. As with any surgery, the amount of time a patient remains in an orthopedic surgery impacts the patient's safety, recovery and medical expenses.

Another typical surgical instrument used in orthopedic surgery involves a rod insertable into the medullary cavity of a bone. These rods are driven into the medullary cavity and used to support a cutting fixture to determine the position and angle of cuts to the bone. However, these rods are unable to self-align within the femur to obtain the optimum alignment to the patient's skeletal structure. Intermedullary rods have been developed that are capable of expanding into the surrounding bone to align and fix the bone. However, these devices fail to conform to the internal dimensions of the medullary cavity, optimize alignment within the bone or provide a single surgical reference point capable of supporting a cutting fixture alignable to the patient for performing multiple orthopedic surgical procedures.

For the foregoing reasons, there is a need for a surgical instrument which would offer relatively high accuracy while providing adjustability to the individual patient. Preferably, the instrument would be capable of performing multiple surgical manipulations based on a single reference point to the patient to enhance accuracy and repeatability. It would be further preferable to provide an instrument that performs multiple functions based on a single fixed support thereby eliminating the need for additional procedures and reducing surgical time, preventing blood loss or infection, reducing anesthesia and eliminating further violation or manipulation of soft tissue or bone. It would be more desirable if the instrument involved minimum complexity so that it can be easily manipulated and implemented. It would also be more desirable to reduce the number of instruments and procedural steps necessary to perform such surgical manipulations.

SUMMARY OF THE INVENTION

The foregoing needs are met by providing a multi-functional surgical tool with various components capable of performing multiple orthopedic surgical functions. The invention relates to an expandable intermedullary support alignable within a medullary cavity of a bone. The support comprises a rod, a plurality of longitudinal roller bearings and a shaft. The rod has a tapered portion defining a longitudinal axis and terminating at a first end thereof. The rod is axially insertable into the medullary cavity and has an outer surface adapted to engage the bone. The rod also has a plurality of longitudinal slots positioned radially about the rod.

The plurality of longitudinal roller bearings are located in a longitudinal slot and movable therein between a collapsed position and an expanded position. At least a portion of each roller bearing is extendable beyond the outer surface of the rod in the expanded position.

The shaft is located in the rod and axially drivable therein. The shaft is adapted to engage the roller bearings. Axial advancement of the shaft moves the roller bearings to the expanded position thereby extending the roller bearings into the bone whereby the support is anchored therein in coaxial alignment therewith. Axial retraction of the shaft moves the roller bearings to the collapsed position thereby releasing the roller bearings from the bone whereby the support is axially removable from the medullary cavity of the bone.

The invention also relates to an orthopedic surgical instrument for resection of a distal end of a femur and a proximal end of an adjacent tibia in preparation for implantation of an orthopedic joint replacement. The instrument comprises an intermedullary support, a cutting guide, a tibial guide and a tibial locking arm. The intermedullary support comprises an alignment rod having a tapered portion terminating at a first end thereof and defining a longitudinal axis therethrough. The rod is axially insertable into the distal medullary cavity of the femur and has an outer surface adapted to engage the femur whereby the rod is alignable within the femur and provides a surgical reference point. The rod has a second end extending a distance beyond the distal femur.

The cutting guide is adjustably mountable to the second end of the rod and positionable about the distal end of the femur. The cutting guide has a plurality of femoral blade slots therethrough. Each femoral blade slot is adapted to operatively receive a blade whereby the blade is guided to perform osteotomies.

The tibial guide is adjustably mountable to the second end of the rod and positionable about the proximal end of the tibia. The tibial guide has a plurality of tibial blade slots therethrough. Each tibial blade slot is adapted to operatively receive a blade whereby the blade is guided to perform osteotomies. The tibial locking arm is slidably movable along the tibial guide and adapted to engage the proximal end of the tibia whereby the tibia is secured relative to the femur.

The invention also relates to a surgical instrument for orthopedic resection of a bone. The instrument comprises an intermedullary support and a cutting guide. The intermedullary support comprises an alignment rod, a plurality of longitudinal roller bearings, and an internal shaft. The alignment rod defines a longitudinal axis and has a tapered portion terminating at a first end thereof coaxially insertable into the medullary cavity of the bone and a second end extending beyond the bone. The tapered portion has an outer surface adapted to engage the bone and defines a plurality of longitudinal slots therethrough positioned radially thereabout. Each roller bearing is located in a longitudinal slot and movable therein between a collapsed position and an expanded position. The internal shaft is axially movable within the rod and adapted to engage the roller bearings. At least a portion of each roller bearing extends a distance beyond the outer surface of the rod in the expanded position. Axial advancement of the shaft moves the roller bearings to the expanded position thereby extending the roller bearings into the bone so that the support is anchored therein in coaxial alignment therewith whereby the rod provides a surgical reference point.

The cutting guide is adjustably mountable to the second end of the rod and positionable about an end of the bone. The cutting guide having a plurality of blade slots therethrough, each blade slot adapted to operatively receive a blade whereby the blade is guided to perform osteotomies.

Finally, the invention relates to a method of resectioning a distal end of a femur and a proximal end of an adjacent tibia in preparation for implantation of orthopedic joint replacements. The method comprises several steps: The expandable intermedullary alignment rod is inserted into the distal medullary cavity of the femur. The rod has a second end opposite the first end, the second end thereof extending beyond the medullary cavity to provide a surgical reference point. The rod is expanded into the bone whereby the rod is alignable thereto and securable therein. A tibial guide having tibial blade slots therethrough is mounted to the second end of the rod. A locking arm is slidably positioned along the tibial guide adjacent the proximal end of the tibia whereby the tibial guide is secured adjacent the tibia and the tibia is secured relative to the femur. A surgical blade is inserted into the tibial blade slots whereby the blade is guided to perform osteotomies. An adjustable cutting guide having femoral blade slots therethrough is mounted onto the second end of the rod adjacent the distal end of the femur. The blade is inserted into the femoral blade slots whereby the blade is guided to perform osteotomies.

BRIEF DESCRIPTION OF THE DRAWINGS

FIG. 4 is a cross-sectional view taken along line 6—6 of FIG. 3 showing the expandable intermedullary support in the expanded position.

FIG. 5 is a cross-sectional view taken along line 6—6 of FIG. 3 showing the expandable intermedullary support in the collapsed position.

DETAILED DESCRIPTION OF THE INVENTION

Figure 1:
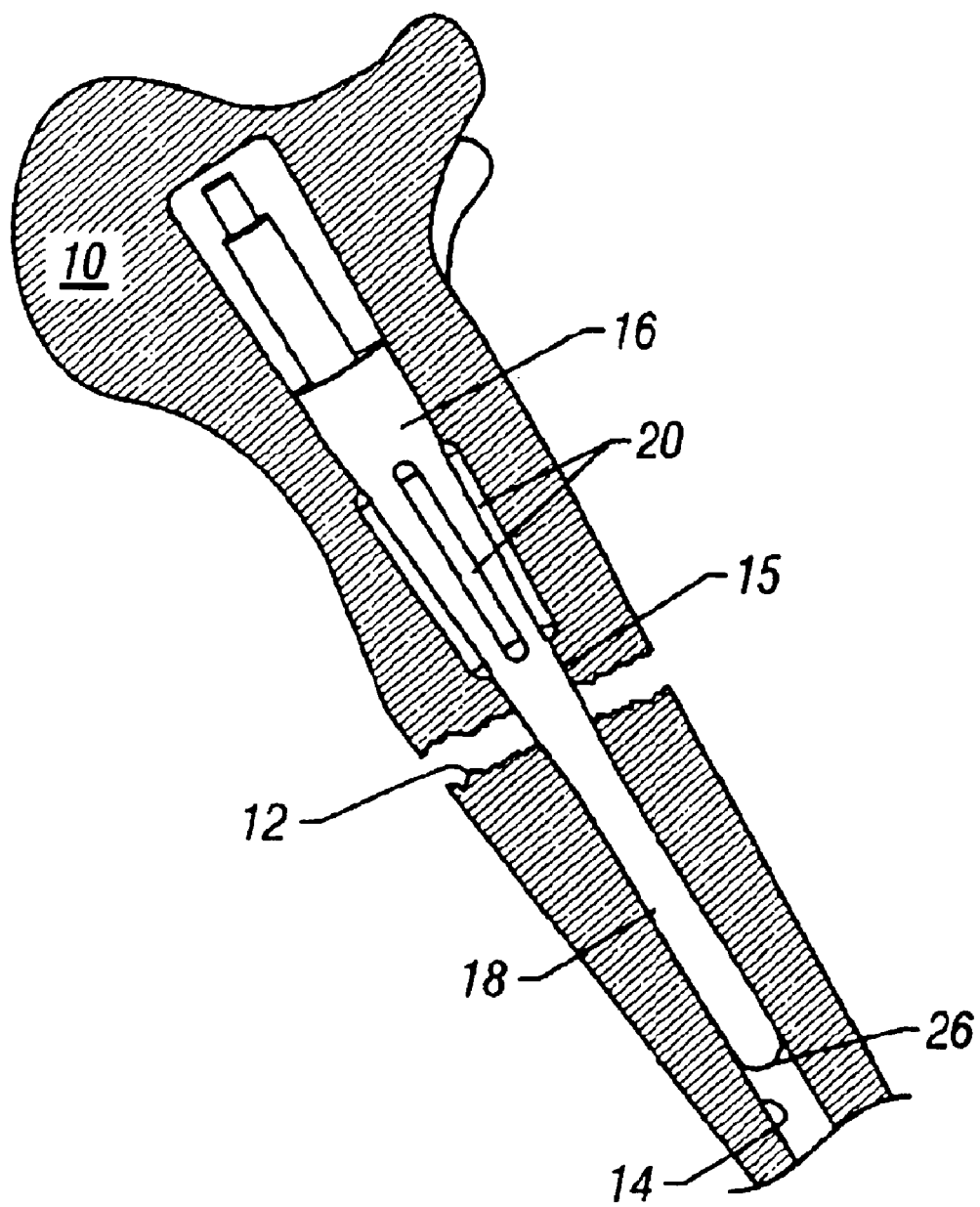
FIG. 1 is schematic cross-section of a patient's humerus with an expandable intermedullary support of a multi-functional orthopedic surgical instrument implanted therein to act as a support for fixation of a fracture in the humerus.

Reference is now made to the present preferred embodiment of the invention, an example of which is illustrated in the drawings provided herein.

The present invention has the following component parts used to perform various orthopedic surgical functions: an expandable intermedullary support, a major cutting guide, a minor cutting guide and a tibial cutting guide. These parts alone, or in combination, enable a surgeon to accurately and easily perform multiple surgical tasks, such as fixation of fractures, resectioning of bones and surgical implantation of joint replacements. As provided herein, the instrument may be used to perform orthopedic surgical operations on the femur, tibia and knee joints of a human. It will be understood that the surgical instrument may also be used for performing surgical operations on various bones and/or joints in humans or other mammals. Desirably, the instrument is adaptable to the surgical needs of the surgeon and/or the anatomy of the patient. A preferred embodiment may comprise one or more of the component parts to perform one or more surgical tasks.

Referring now to the drawings in general and to FIG. 1 in particular, the humerus bone 10 of a human patient is shown. The bone 10 has a medullary cavity 14 extending axially therethrough and a fracture 12 therethrough. Implanted within the medullary cavity 14 of bone 10 is the preferred embodiment of the expandable intermedullary support 16.

Figure 6:
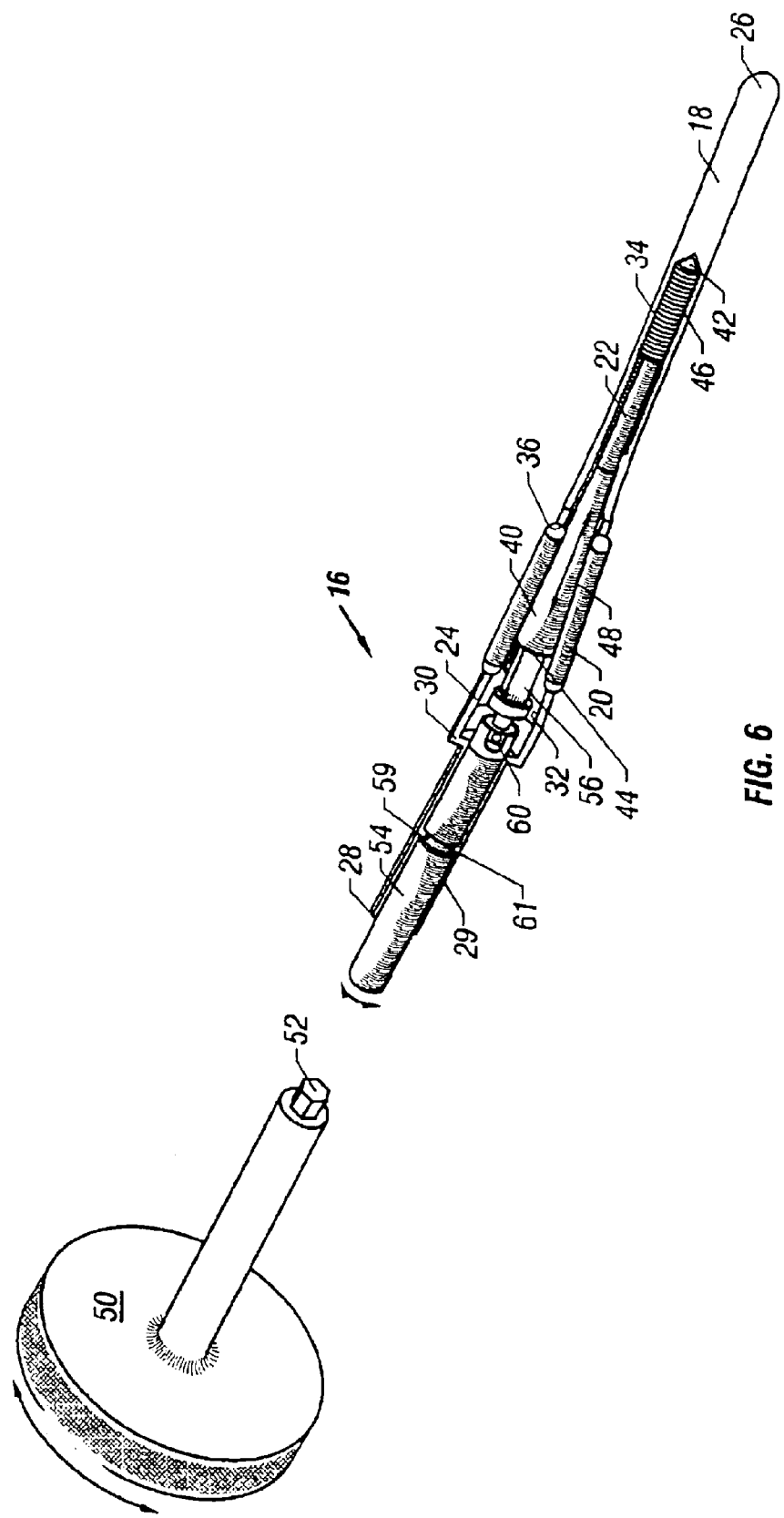
FIG. 6 is a perspective view showing the expandable intermedullary support of FIG. 4 and an actuator used in combination therewith.

The support 16 comprises a rod 18, a plurality of longitudinal roller bearings 20, and an internal shaft 22 (shaft is shown in FIGS. 4–6).

The support 16 is disposed in the proximal humerus and implanted therein. As discussed more fully herein with respect to FIG. 12, a reamer may be used to drill or ream out the medullary cavity so that it is adapted to receive and/or conform to the shape of the support 16. Alternatively, the support 16 may be driven into the medullary cavity 14. As the tissue of the medullary cavity is displaced, an inner surface 15 is defined within the bone 10.

Figure 7:
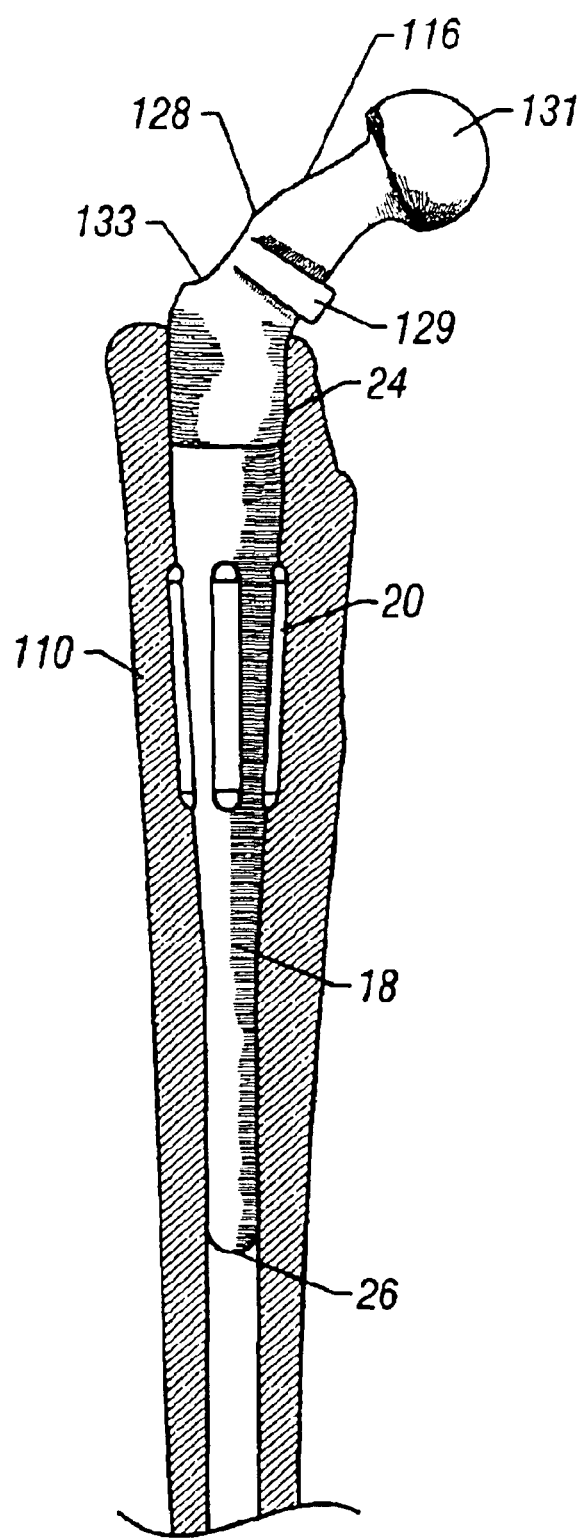
FIG. 7 is a schematic cross-section of a patient's femur with another embodiment of the expandable intermedullary support of FIG. 1 implanted in the proximal femur for total joint replacement.
Figure 8:
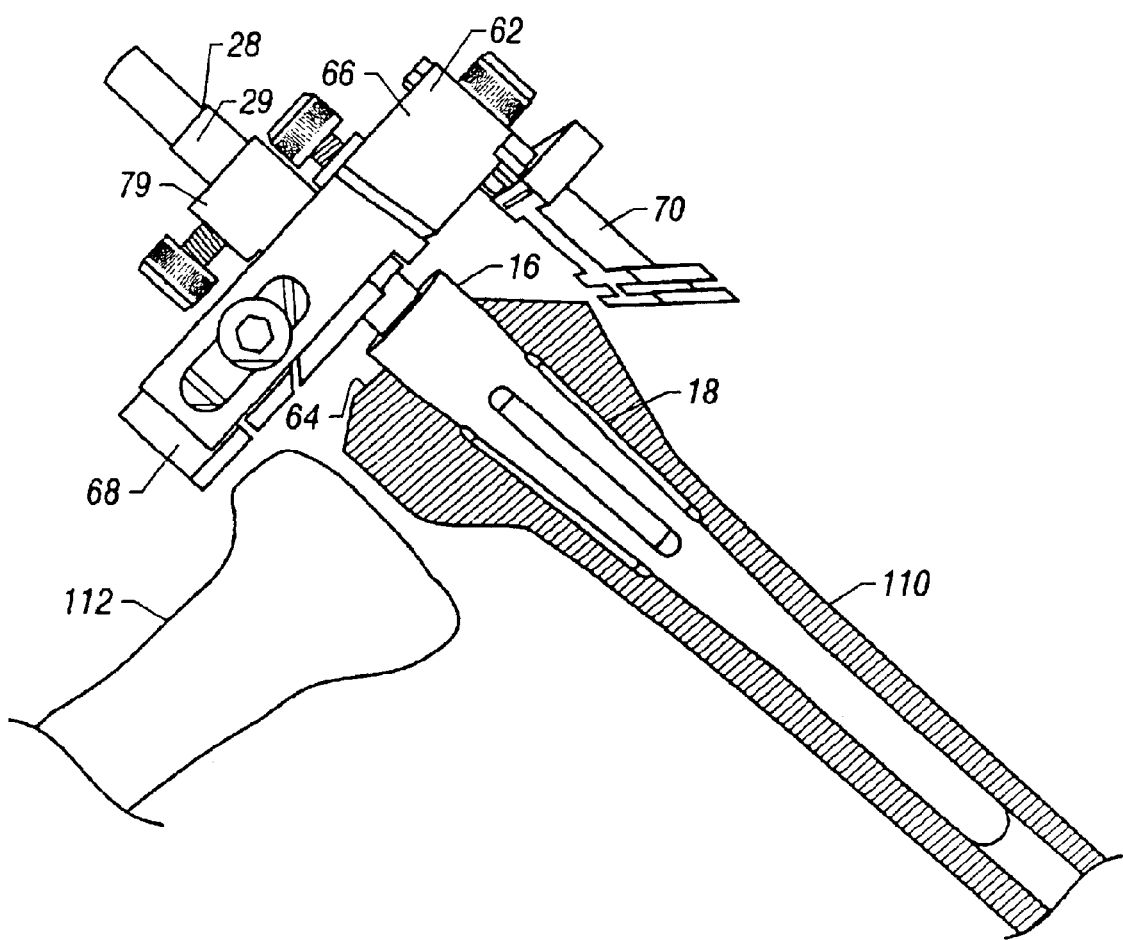
FIG. 8 is a side view of the multi-functional orthopedic surgical instrument showing a major cutting guide mounted to the expandable intermedullary support of FIG. 3 inserted in the distal femur of a patient.
Figure 12:
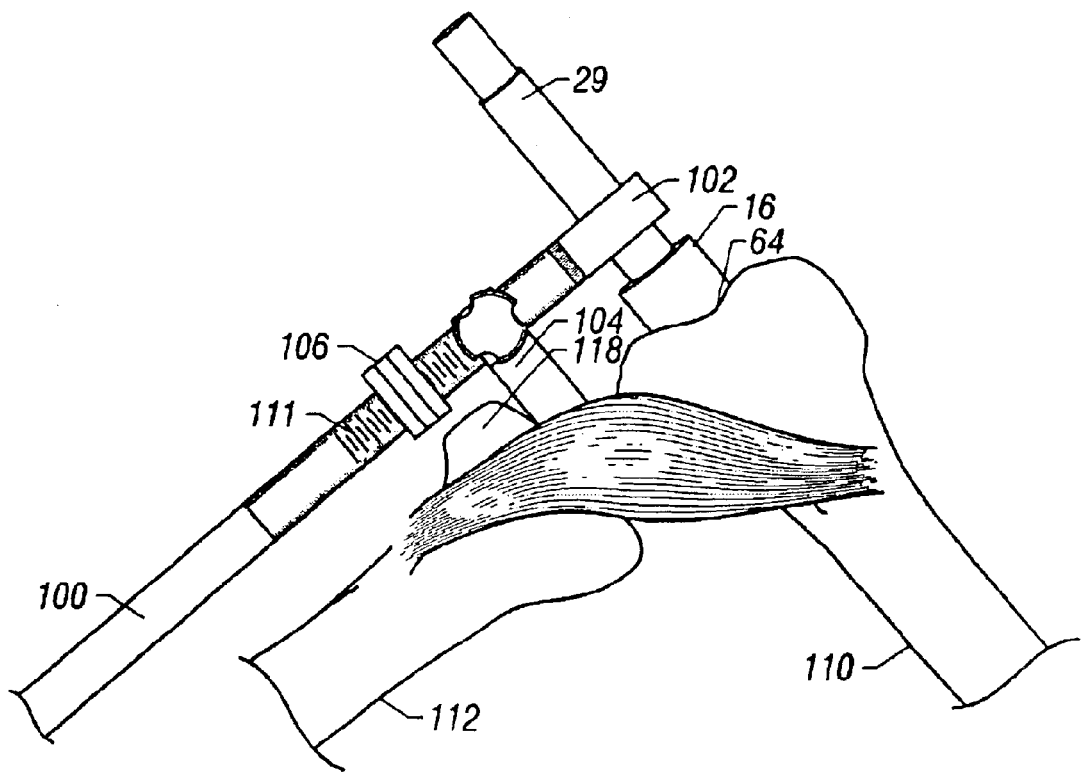
FIG. 12 is a side view of the multi-functional orthopedic surgical instrument showing a tibial guide mounted to the expandable intermedullary support of FIG. 8.

As seen in FIG. 1, the support 16 is inserted into the bone 10 and implanted therein. The support 16 may be permanently or temporarily implanted within a bone, to provide internal support and/or internally align fractures as will be understood by one skilled in the art. The support 16 may also be partially inserted into the medullary cavity 14 such that a portion of the support extends beyond the bone as depicted in FIGS. 7, 8 and 12, as will be discussed more fully herein.

Referring now to FIGS. 2 through 6, the rod 18 of FIG. 1 is shown in greater detail. The rod 18 preferably has a tapered portion 24 terminating at a first end 26, a second end 28 opposite the first end 26 and a shank portion 29 about the second end 28. The tapered portion 24 has an outer surface 30 adapted to engage the inner surface 15 of the bone 10 when inserted into the medullary cavity 14. Desirably, the contour of the rod 18 is shaped to conform to the inside surface 15 of the bone 10 to increase surface contact between the outer surface 30 of the rod 18 and the inner surface 15 of the bone 10. The contour of the rod 18 may be selected to conform to the anatomy of a particular patient's bone(s) or to meet surgical needs.

Figure 2:
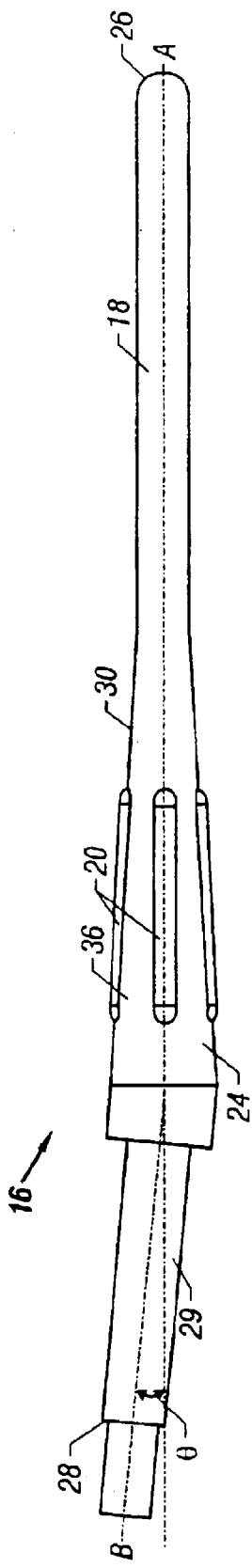
FIG. 2 is a top plan view of the expandable intermedullary support of FIG. 1.
Figure 3:
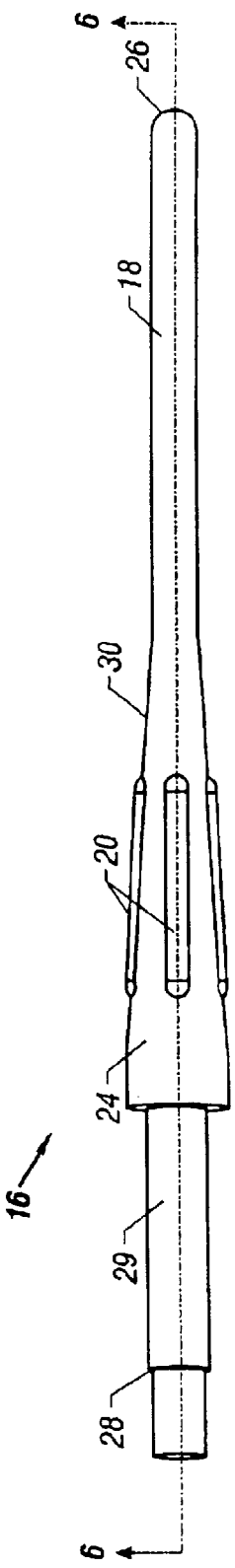
FIG. 3 is a side elevational view of the expandable intermedullary support of FIG. 1.

As shown in FIG. 2, the tapered portion 24 defines a longitudinal axis A preferably positioned coaxial with the femur. The shank portion 29 of the rod 18 has a longitudinal axis B therethrough tilted away from the longitudinal axis A of the tapered portion 24 of the rod 18 at an acute angle θ thereto.

The angle θ of the tapered portion may vary based on the particular application. It will be understood that the desired angle, if any, is dependent on the anatomy of the patient and the bone at issue. For example, as seen in FIG. 2, the desired angle is approximately five (5) degrees. Generally, an angle of about three to seven degrees is used for knee surgeries to conform to the angle of the femur bone to the hip. However, a different angle or no angle at all may be desirable, depending on the surgical needs.

Referring now to FIGS. 4 through 6, the rod 18 has a rod cavity 32 extending inwardly from the second end 28 toward the first end 26. The rod cavity 32 defines a plurality of internal threads 34 axially disposed within the rod 18. The rod 18 is also provided with a plurality of longitudinal slots 36 extending into the rod cavity 32. The longitudinal slots 36 are generally elliptical holes preferably spaced circumferentially about the tapered portion 24 and extending longitudinally about the tapered portion 24 of the rod 18.

The longitudinal slots 36 are adapted to receive the longitudinal roller bearings 20. The roller bearings 20 are cylindrical and slightly larger than the longitudinal slots 36 thereby allowing the roller bearings to enter the longitudinal slots 36 but not escape. Alternatively, other bearings, such as ball bearings, may be positioned in holes and/or slots in the rod to achieve the same result.

The roller bearings 20 are radially movable between a collapsed and an expanded position within the longitudinal slots 36. In the collapsed position (FIG. 5), the roller bearings 20 preferably are positioned at or below the outer surface 30 of the rod 18 so that the rod 18 remains movable within the medullary cavity 14. In the expanded position (FIG. 4), the roller bearings 20 extend beyond the outer surface 30 of the tapered portion 24 thereby increasing the outer diameter D of the tapered portion 24 along the longitudinal slots so that the rod 18 may be expanded into the surrounding bone and anchored therein.

Referring back to FIG. 1, the rod 18 is shown expanded into the bone 10 and anchored therein. The roller bearings 20 are extended into the bone 10 surrounding the rod 18 to fix the rod into place within the bone. The roller bearings 20 extend beyond the rod 18, through the inner surface 15, into the medullary cavity 14 and into the solid portion of the bone. Depending on the patient, the particular bone at issue, the amount of extension of the roller bearings and the extent the medullary cavity has been reamed, the roller bearings may extend into the medullary cavity and/or meet or penetrate solid bone. For simplicity, the phrase "into the bone" will be used to encompass extension of the roller bearings into the medullary cavity, inner surface and/or the bone.

The expansion of the roller bearings 20 into the bone creates a rigid compression fit or fixation which may be used to secure the support in the bone, align bone fragments and/or insert joint replacements. Preferably, the longitudinal slots 36 are evenly dispersed about the rod 18 to enable the roller bearings 20 to symmetrically expand into the bone thereby centering the rod 18 within the medullary cavity 14 and aligning it therein. Alternatively, the longitudinal slots 36 may be spaced or the roller bearings 20 extended to create an offset of the rod 18 within the rod cavity 32. This may also be achieved by extending only some roller bearings 20 on one side of the rod 18, or by extending certain roller bearings 20 more than others.

Referring back to FIGS. 4 through 6, the shaft 22 is located within the rod cavity 32 in axial alignment with the rod 18. The shaft 22 has an elongate body portion 40, a tip 42 and a rear end 44 opposite the tip. The rod 18 is longitudinally disposed within the rod cavity 32 with the tip 42 towards the first end 26 of the rod 18, and the rear end 44 towards the second end 28 of the rod 18. The tip 42 has a plurality of threads 46 threadably connected to the internal threads 34 of the rod 18. In the preferred embodiment, the shaft 22 is axially movable within the rod cavity 32 as indicated by the linear double headed linear arrows (FIG. 6). The shaft 22 has a tapered outer surface 48 adapted to engage the roller bearings 20 so that, as the shaft 22 is axially advanced within the rod 18, the shaft 22 contacts the roller bearings 20 and extends the roller bearings 20 radially through the longitudinal slots 36 in the rod 18 (FIG. 4). As the shaft 22 is retracted, the roller bearings 20 are released to fall back to the collapsed position (FIG. 5). As shown in FIGS. 4 through 6, the tapered outer surface 48 of the shaft 22 conforms to the shape of the rod 18 and enables the shaft 22 to uniformly engage the roller bearings 20 and extend them radially outward. The shaft 22 may be provided with any body shape which permits the roller bearings 20 to be extended and collapsed to the desired position.

As best seen in FIG. 6, an actuator 50 may be provided to axially drive the shaft 22 and expand the roller bearings 20. The rear end 44 of the shaft 22 is adapted to receive an actuator 50 for driving the shaft 22 axially within the rod 18. As shown in FIG. 6, the actuator 50 may be an allen wrench having an bit 52 connectable to the second end of the shaft 22 by a socket 54 and capable of imparting a rotational force to the shaft 22 as indicated by the curved double-headed arrows. One or more extensions, linkages and/or sockets may be used to connect the actuator to the shaft, or the actuator may be directly connected to the shaft. Other driving tools may be used in place of the actuator as shown, such as ratchets, wrenches, drills, screw drivers, or other devices known to those skilled in the art to perform the function of driving the shaft.

As shown in FIGS. 4 through 6, a socket 54 is provided adjacent the second end 44 of the shaft 22. The socket 54 comprises a key 56, a receptacle 58 and a link 60 therebetween. The socket 54 is rotatable within the rod 18 as indicated by the curved double-headed arrows (FIG. 6) and transfers the rotational force of the actuator 50 to the shaft 22. The receptacle 58 is adapted to receive the actuator 50 and rotate therewith. The receptacle 58 has a recess 59 corresponding to an internal lip 61 in the rod 18 which allows the socket 54 to rotate, but prevents the socket from moving axially within the rod 18. The key 56 has a polygonal cross-section insertable into the mated second end 44 of the shaft 22. The key 56 is adapted to operatively engage the second end 28 of the shaft 22 so that rotation of the key 56 rotates the shaft 22 while allowing the shaft 22 to slidably movable along the key 56. The link 60 permits the key 56 and the receptacle 58 to negotiate angles in the rod 18 so that the rotational force of the actuator 50 may be transferred from the actuator 50 around non-linear portions of the rod 18, such as shank portion 29, to the shaft 22.

The socket 54 may comprise multiple linkages, joints and other components of various sizes to allow the rotational force to extend from the actuator to the shaft. Alternatively, the actuator may be directly linked to the second end of the shaft, usually when the tilt angle is zero an no extension is necessary (as in FIG. 7).

FIG. 7 shows another embodiment of the intermedullary support 116 disposed in a femur 110 of a patient for total joint replacement of a patient's hip. As with the support 16 previously described, the support 116 preferably has a rod 18, plurality of longitudinal rollers 20, a tapered portion 24 terminating at a first end 26, and a second end 28 opposite the first end 26. Essentially, the embodiment of intermedullary support 116 shown in FIG. 7 is the same as the intermedullary support 16 of FIGS. 1 through 6, except that it is further provided with a curved shank 129 and a joint implant 131 extending from the shank. Additionally, the embodiment of FIG. 7 differs from the embodiment of FIGS. 1 through 6 in that it has no socket 54 and the tilt angle θ is zero. The actuator 50 may be directly inserted into actuator hole 133 and connected to the shaft (not shown). The actuator 50 is then rotated to expand the rollers 20 into the bone 110 to fix and align the support 116 within the bone as previously described.

The joint implant 131 of FIG. 7 is a ball and socket joint adapted to replace the hip joint of a patient when the support 116 is inserted into the proximal femur. The hip joint is replaced by temporarily or permanently inserting the support 116 into the medullary cavity of the proximal femur and expanding the support 116 therein. The support 116 is fixedly positioned within the proximal femur with the joint implant 131 positioned to function in place of the patient's hip joint. While the support 116 is depicted in FIG. 7 as a replacement for the hip join, it will be understood that the support 116 may be adapted for insertion into any bone and/or provided with a joint implant 131 shaped to conform to and replace other joints in the body.

Referring now to FIG. 8, the major cutting guide 62 is shown mounted to the expandable intermedullary support 16 inserted into the distal end of a patient's bone 110 for performing osteotomies. The second end 28 of the rod 18 extends beyond the distal end 64 of the femur bone 110 to act as a base for the major cutting guide 62. The major cutting guide 62 is mounted on the shank portion 29 of the rod 18 and positioned adjacent the distal end 64 of the bone 110 and the proximal end of an adjacent tibia 112. While this embodiment shows the preferred embodiment of the major cutting guide 62 in combination with the expandable support 16 adjacent a distal femur and adjacent tibia, it will be understood that the major cutting guide 62 may be mounted to any bone on any device connectable to the desired bone, such as rods, skewers, bolts, and other devices that provide an anchor in the intermedullary cavity to support the cutting guides.

Figure 9:
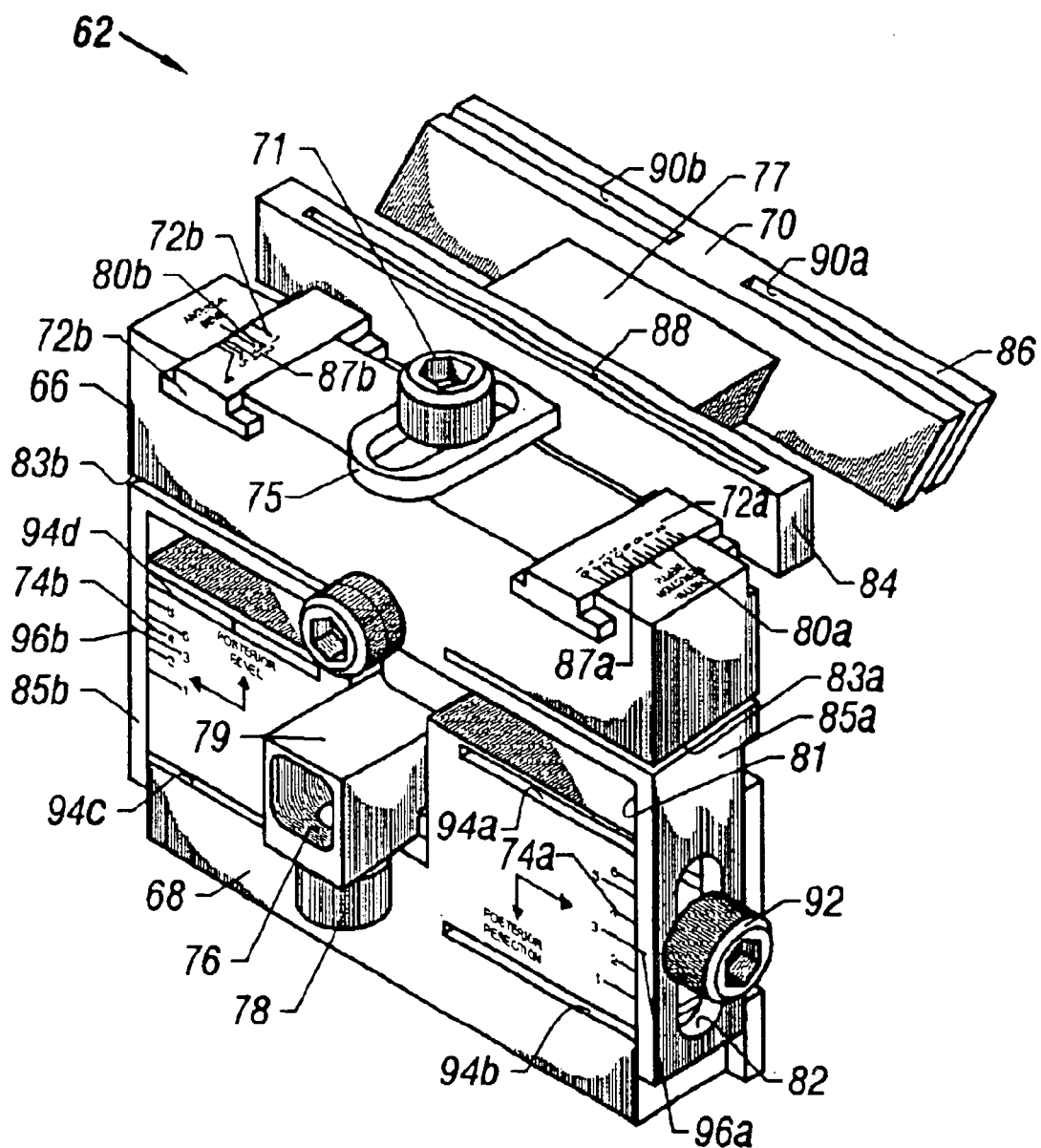
FIG. 9 is a perspective view of the major cutting guide of FIG. 8.

As shown in greater detail in FIG. 9, the major cutting guide 62 is a device which is made of several adjustable blocks or plates with blade slots for making precision cuts to the bone (osteotomies). The major cutting guide 62 has a posterior template 68, a distal template 70, and a guide member 66 therebetween. The major cutting guide 62 is mounted onto the support 16 and positioned about the bone. The major cutting guide 62 is slidably positionable along the shank portion 29 of the rod 18 and secured thereto.

Guide member 66 has a generally planar body, a duct 79 therein, dual tracks 80a and 80b, blade slots 83a and 83b and dual extensions 85a and 85b. The duct 79 defines an aperture 76 adapted to slidingly receive the shank portion 29 of the rod 18. Locking bolt 78 in duct 79 secures the guide member 66 to the shank portion 29 of the rod 18. The guide member 66 is provided with blade slots 83a and 83b adapted to receive and guide a surgical cutting instrument, such as a saw, scalpel, blade or other tool which may be used for performing osteotomies as will be understood by one skilled in the art. While various shapes and angles of blade slots are depicted herein, it will be understood that the blade slots may be of various dimensions and angles as necessary to perform the desired cuts using cutting instruments known to those of skill in the art.

The extensions 85a and 85b are positioned on opposite sides of and extend away from the body of the guide member 66. The extensions 85a and 85b form a channel 81 adapted to receive the posterior template 68. Extension 85a has a slot 82 with a locking bolt 92 therethrough to secure the posterior template 68 in position within channel 81. Extensions 85a and 85b have markings 96a and 96b corresponding to markings on the posterior template 68 to determine the desired position of the posterior template 68 to the guide member 66. Rails 72a and 72b are disposed in the guide member 66 on the opposite side of the body from the extensions 85a and 85b. The tracks 80a and 80b define channels adapted to slidingly receive the rails 72a and 72b of the distal template 70 as will be described more fully herein.

The posterior template 68 has a generally planar body with a plurality of blade slots 94a, 94b, 94c and 94d therethrough, and posterior gauges 74a and 74b thereon. The posterior template 68 is slidably positionable between the extensions 85a and 85b of the guide member 66. The posterior template 68 is connected to the guide member 66 by locking bolt 92. The posterior gauges 74a and 74b are positioned along opposite sides of the posterior template and correspond to markings 96a and 96b on the guide member 66. The posterior gauges 74a and 74b are used to measure the position of the posterior template 68 to the guide member 66 and determine the position of the blade slot relative to the intermedullary support 16.

As shown in FIG. 9, the distal template 70 is positioned substantially perpendicular to the posterior template 68 and connected to the guide member 66 by locking bolt 71. The distal template 70 is provided with a first slotted member 84, a second slotted member 86, and a body portion 77 therebetween. The distal template 70 is further provided with a slotted tab 75 and dual rails 72a and 72b extending from the first slotted member 84 and positioned adjacent the guide member 66. The dual rails 72a and 72b are inserted into and slidably positionable along the corresponding tracks 80a and 80b in the guide member 66. The rails 72a and 72b are provided with distal gauges 87a and 87b to measure the position of the distal template 70 to the guide member 66. The first slotted member 84 of the distal template 70 has a blade slot 88 therethrough substantially parallel to the posterior template 68. The second slotted member 86 has blade slots 90a and 90b therethrough at an acute angle to the posterior template 68.

Figure 10:
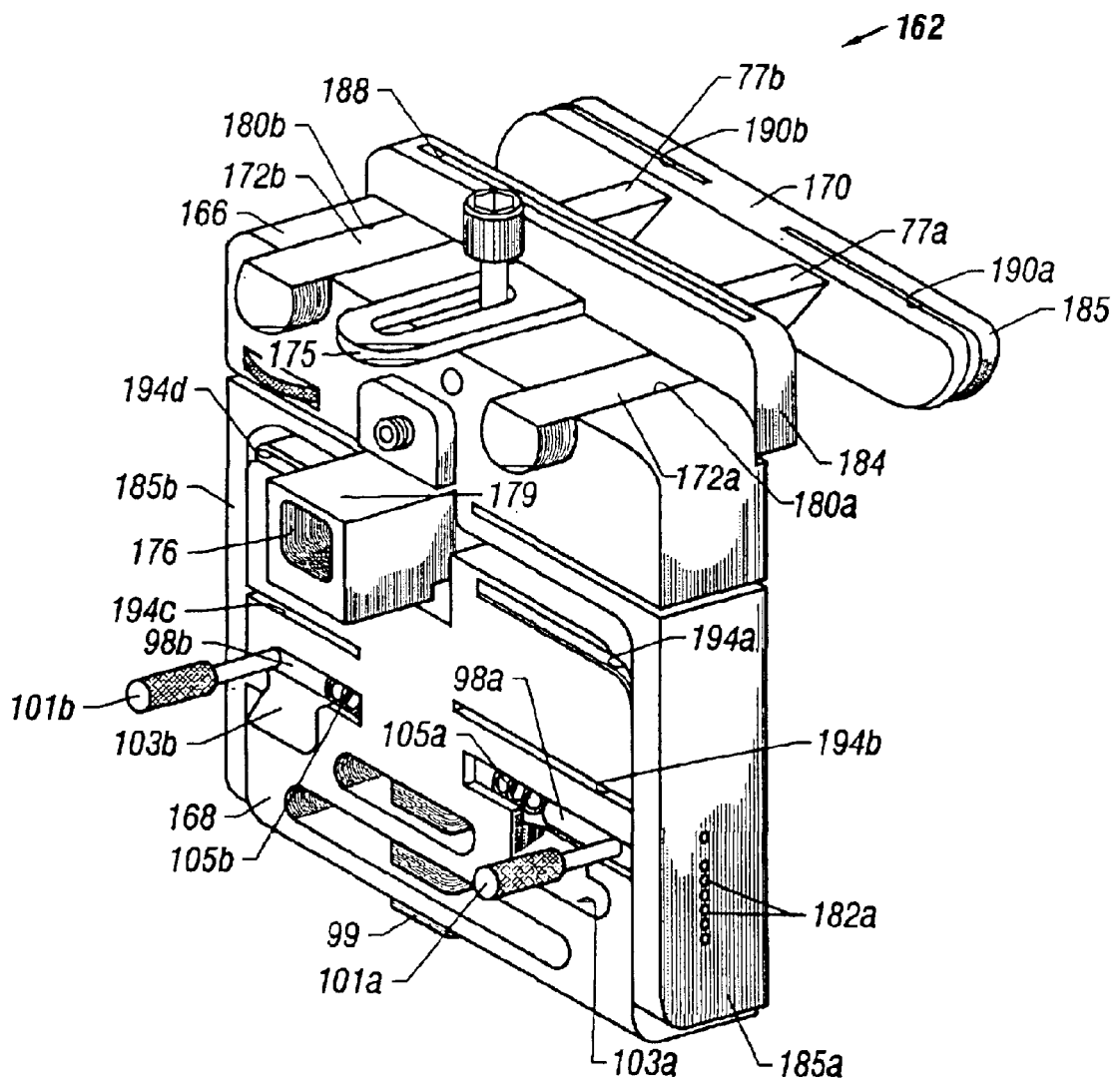
FIG. 10 is a perspective view of an alternative embodiment of the major cutting guide of FIG. 9.

FIG. 10 shows another embodiment of the major cutting guide 162. This embodiment shows an alternate form of the apparatus with various different aspects, such as alternate connectors, adjusters, and templates. The major cutting guide 162 has a posterior template 168, a distal template 170, and a guide member 166 therebetween. The posterior template 168 has a pair of grooves 103a and 103b with springloaded pegs 98a and 98b therein and levers 101a and 101b extending therefrom. The posterior template 168 has four blade slots 194a, 194b, 194c and 194d therethrough. The guide member 166 has a duct 179, dual extensions 185a and 185b and tracks 180a and 180b. The distal template 170 has a first slotted member 184 with blade slot 188 therethrough, a second slotted member 185 with dual blade slots 190a and 190b therethrough, a pair of legs 77a and 77b therebetween. A pair of rounded rails 172a and 172b and a slotted tab 175 extend from the first slotted member 184. Hole 182a is shown in extension 185a, but the corresponding hole 182b in extension 185b is not shown.

The major cutting guide 162 has an aperture 176 in duct 179 adapted to receive the shank portion 29 of the rod 18 so that the major cutting guide 162 is slidably positioned along the shank portion 29 of the rod 18 as in the embodiment of FIGS. 8 and 9. In the embodiment of FIG. 10, however, the posterior template 168 has a pair of springloaded pegs 98a and 98b extending into holes 182a and 182b in the extensions 185a and 185b. The posterior template 168 is still slidably positionable with respect to the guide member 166 between extensions 185a and 185b; however, in this embodiment, the pegs 98a and 98b may be contracted and released to the control the movement of the posterior template 168.

Levers 101a and 101b are disposed in grooves 103a and 103b and used to move the pegs 98a and 98b inward and release them from holes 182a and 182b in the extensions 185a and 185b. The grooves 103a and 103b are shaped to retain the levers 101a and 101b in the desired position. Once the posterior template 168 is in the desired position, the pegs 98a and 98b are released to extend into the holes 182a in the extensions 185a and 185b to secure the posterior template in position. The force of springs 105a and 105b drive the pegs into the holes 182a and 182b along the extensions 185a and 185b. Additional variations, such as curvature of the various components of the cutting guide, may also be employed.

Figure 11:
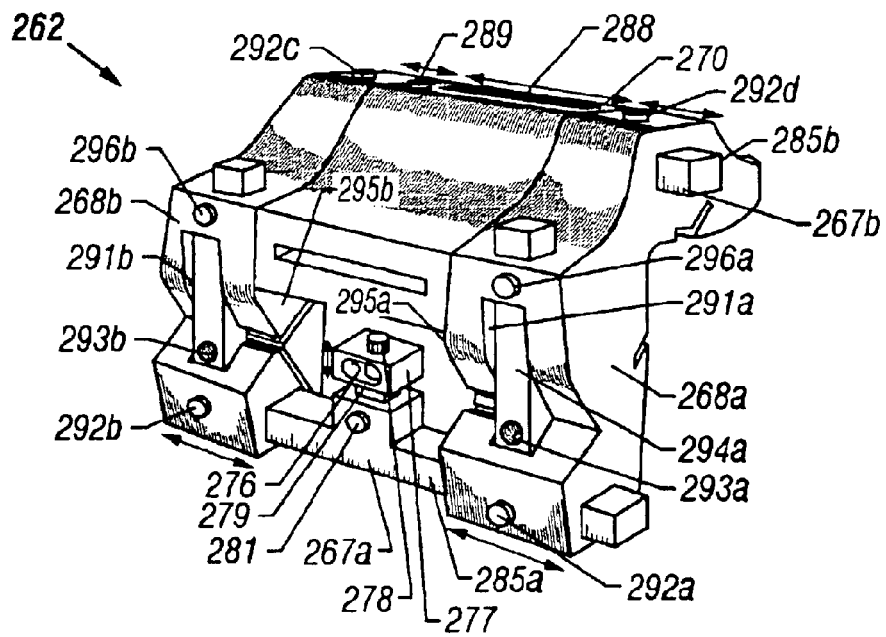
FIG. 11 is a perspective view of a minor cutting guide.

FIG. 11 shows a minor cutting guide 262 that may be used in combination with the intermedullary support 16 for performing osteotomies, such as the intracondylar notch. The minor cutting guide 262 has parallel beams 285a and 285b, a mount 277, two parallel cutting arms 268a and 268b and a distal minor cutting guide 270. Mount 277 is connected to beam 285a and the cutting arms 268a and 268b are slidably positionable along beams 285a and 285b. Distal minor cutting guide 270 is positioned along beam 285b between the cutting arms 268a and 268b. Beam 285a is provided with a scale 267a and beam 285b is provided with a scale 267b for measuring the position of the various components along the beams.

As with the cutting guides of FIGS. 8 through 10, the minor cutting guide 262 is slidingly positionable on the shank portion 29 of the rod 18 by disposing the shank portion 29 through an aperture 276 in mount 277 and tightening locking bolt 278. Mount 277 is connected to beam 285a via telescoping arm 279 and secured in position with set screw 281. Telescoping arm 279 linearly extends and retracts mount 277 relative to beam 285a.

The cutting arms 268a and 268b may be secured in position relative to rod 18 by slidably positioning the cutting arms 268a and 268b along the beams 285a and 285b. The cutting arms 268a and 268b may be secured into position with set screws 292a, 292b, 292c and 292d. The cutting arms 268a and 268b each define an inner cutting surface 295a and 295b for guiding a surgical instrument to perform osteotomies.

Similarly, the distal minor cutting guide 270 preferably is located between the cutting arms 268a and 268b and slidably positionable along beam 285b. The distal minor cutting guide 270 preferably has a blade slot 288 therethrough for guiding a surgical instrument to perform osteotomies. The distal minor cutting guide 270 is also provided with a set screw 289 for securing the distal minor cutting guide 270 in position along the beam 285b.

The cutting arms 268a and 268b have drill slots 291a and 291b therethrough. Drill guide 294a is slidably positionable within drill slot 291a and has a drill hole 293a therethrough. Drill guide 294b is slidable positionable within drill slot 291b and has a drill hole 293b therethrough. The drill guides 294a and 294b may be secured into the desired position within their drill slots via set screws 296a and 296b respectively. Adjustable drill holes 293a and 293b may be used to drill fenestrations into the bone if necessary.

Referring now to FIG. 12, a tibial cutting guide 100 is shown adjacent a patient's proximal tibia 112 and supported on the expandable support 16. The tibial cutting guide 100 comprises a tibial guide member 102, a tibial locking arm 104 and a tibial template 106. The tibial cutting guide 100 locks the tibia 112 in position at an angle (preferably perpendicular) to the adjacent femur bone 110 in preparation for surgeries, such as osteotomies and/or knee replacements.

Figure 13:
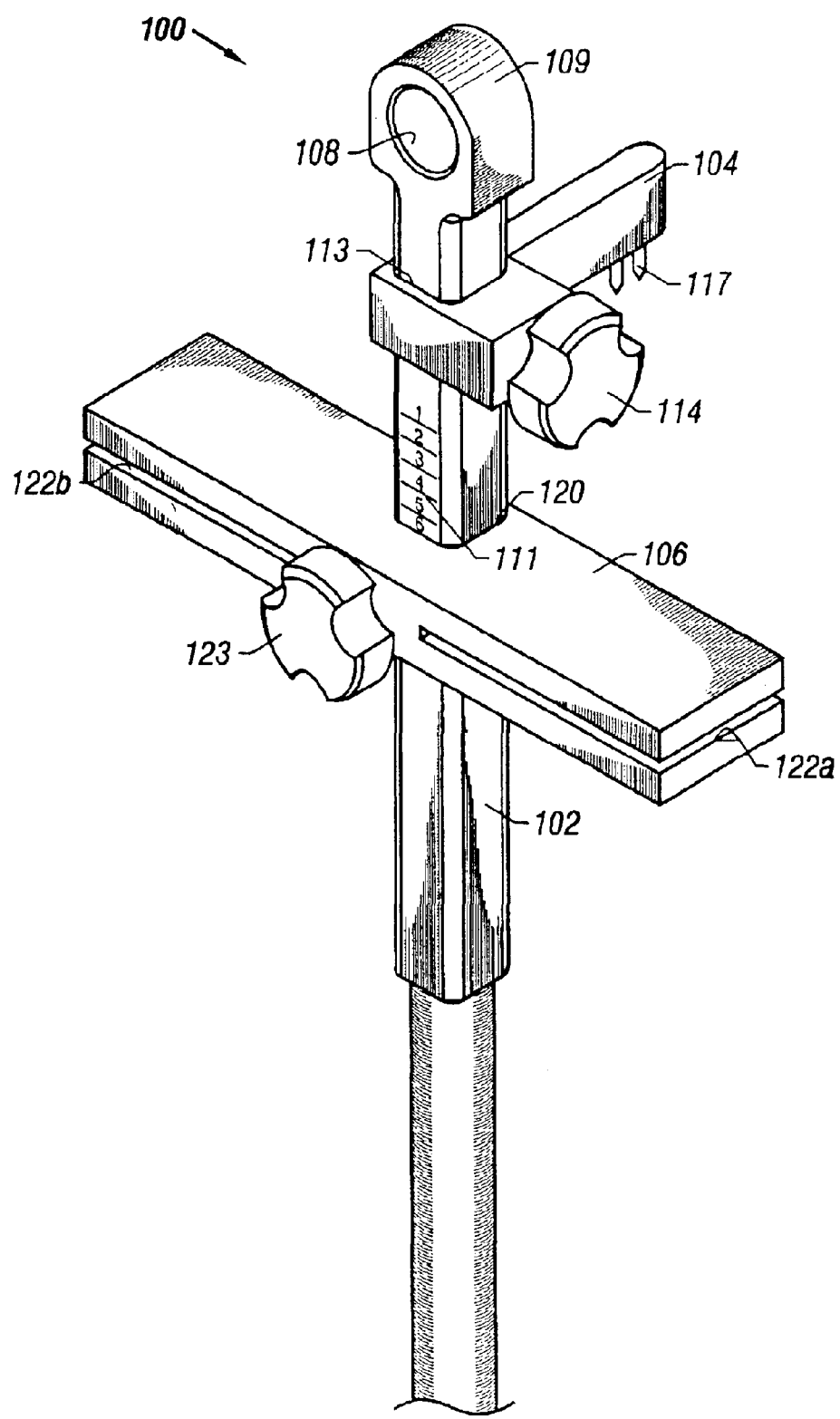
FIG. 13 is a perspective view of the tibial cutting guide of FIG. 12.

As best seen in FIG. 13, the tibial guide member 102 has an elongate body and an aperture 108 at a first end 109 thereof. The aperture 108 is adapted to receive the shank portion 29 (shown in FIG. 12) of the rod 18 so that the tibial guide member 102 is slidably positionable along the shank portion 29 of the rod 18 adjacent the distal end 64 of the bone 110. When mounted on the support 16, the tibial guide member 102 preferably is positioned adjacent the tibia 112 and substantially parallel thereto. The guide member 102 has tibial gauges 111 comprising incremental markings for positioning the tibial template 106.

As shown in FIG. 13, the tibial locking arm 104 has an aperture 113 adapted to receive the tibial guide member 102. The tibial template 106 is slidably positionable on the guide member 102 and secured in place at the desired position along the tibial gauge 111 via locking bolt 114. The aperture 113 is preferably shaped to conform to the shape of the tibial guide member 102 so that the tibial locking arm 104 may slidably move thereon. The tibial locking arm 104 has fixation pegs 117 to secure the locking arm 104 in the desired position adjacent the proximal end 118 of the tibia 112. As seen in FIG. 12, the tibial locking arm 104 extends away from the tibial guide member 102 and is positioned between the tibia 112 and femur 110. The tibial locking arm 104 is connected to the proximal end 118 of the tibia 112 into pre-drilled fenestrations (not shown). The pegs 117 are threadably connected to pre-drilled fenestrations located in the proximal end 118 of the tibia 112 to secure the tibial locking arm 104 to the patient's of the tibia 112. In this position, the patient's tibia 112 is effectively secured perpendicular to the patient's adjacent bone 110.

The tibial template 106 preferably has a generally rectangular body with an aperture 120 and tibial blade slots 122a and 122b therethrough. The tibial blade slots 122a and 122b preferably are parallel to the proximal end 118 of the tibia 112 and bisect the tibial template 106. The tibial blade slots 122a and 122b are adapted to receive a surgical cutting instrument to perform tibial osteotomies as will be understood by those of skill in the art.

While all of the blade slots and/or surfaces of the major cutting guides 62 and 162, the minor cutting guide 262 and the tibial cutting guide 100 are depicted at specific angles, shapes and position, the blade slots may vary depending on the surgical needs. Moreover, a variety of cutting guides and templates of various sizes, cutting angles, and dimensions may be used in accordance with the present invention. One or more cutting guides may be used on a single patient to perform multiple osteotomies.

Figure 14:
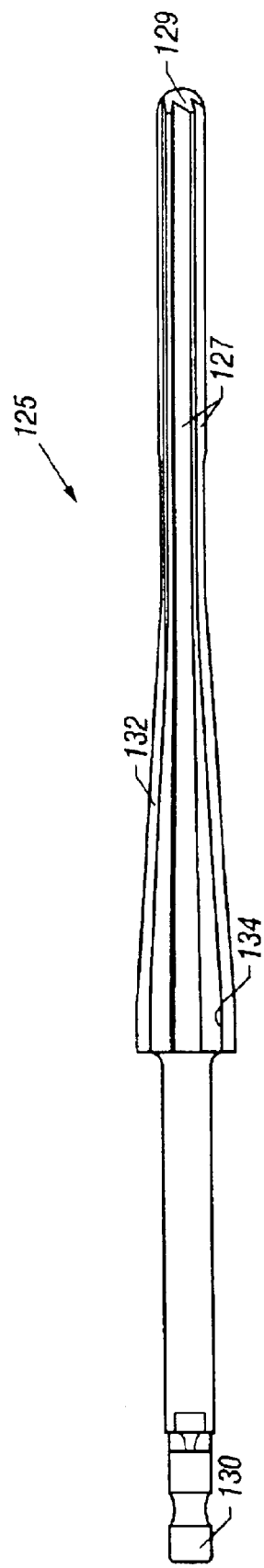
FIG. 14 is a side elevational view of a reamer used in conjunction with the present invention.

Referring to FIG. 14, a reamer 125 for use with the present invention is shown. The reamer 125 has an elongate tapered body, a plurality of longitudinal drilling blades 127, a tip end 129 and an opposite rear end 130. Preferably, the reamer 125 has a tapered portion 132 shaped similar or complementary to the tapered portion 24 of the rod 18. The longitudinal drilling blades 127 extend longitudinally along the tapered portion 132 of the reamer 125. Grooves 134 are provided between the blades 127 to enhance the drilling operation. The rear end 130 is adapted to operatively receive a rotational tool, such as the actuator 50, a rotational drill or other mechanical device for rotationally driving the reamer. The reamer 125 is drivable into the medullary cavity 14 of a patient's bone 10 to remove tissue from the medullary cavity 14 and/or surrounding bone to create a pocket adapted to receive the expandable support 16. The reamer 125 may also be used to drill out other bones in preparation for other supports, such as support 116 in bone 110.

In operation, the support 16 is inserted into the medullary cavity 14 of a bone 10 of a patient. The first end 26 of the rod 18 is axially inserted into the distal end 64 of the bone, as shown in FIG. 1. The rod 18 may be driven axially into the medullary cavity 14 of the bone, or the medullary cavity 14 may be pre-drilled by the reamer 125 for easier insertion and/or better fit. The support 16 (or support 116) may be axially driven into the bone and: 1) implanted therein to repair fractures or provide internal support as seen in FIG. 1; 2) partially inserted to act as a joint replacement as shown in FIG. 7; 3) inserted in a bone to support the cutting guide as shown in FIG. 8; and/or 4) partially inserted into a bone to support the tibial cutting guide 100 as shown in FIG. 12.

Once the support 16 (or 116) is inserted into the medullary cavity 14, the actuator 50 may then be used to rotationally drive the shaft 22 along the internal threads 34 of the rod 18. The actuator 50 rotates the shaft 22 so that the shaft 22 is driven along the internal threads 34 of the rod 18. As the shaft 22 moves along the threads 34, the shaft is driven axially within the rod 18. As the shaft 22 is axially advanced towards the first end 26 of the rod 18, the outer surface 48 of the shaft 22 engages the longitudinal roller bearings 20 and drives them radially outward to the expanded position. The longitudinal roller bearings 20 increase the effective diameter of the rod along the tapered portion 24 as they extend into the bone. Preferably, the roller bearings 20 extend uniformly about the tapered portion 24 thereby centering the rod 18 and placing the rod 18 in substantial coaxial alignment with the bone.

The major cutting guide may be connected to the support 16 to perform surgeries such as osteotomies. The support 16 is inserted into the distal femur 110 such that the second end 28 extends beyond the distal end 64 of the femur 110 and provides a surgical reference point (FIG. 7). The major cutting guide 62 (or 162) is slidably mounted to the support 16 adjacent the distal end 64 of the bone 110 by disposing the shank portion 29 of the rod 18 through the duct 79 and tightening locking bolt 78. The posterior template 68 may then be positioned along the guide member 66 based on the posterior gauges and secured in position with locking bolt 92. The distal template 70 may also be positioned along the guide member based on the distal gauges and secured in position with locking bolt 71. Once in position, a surgical blade may be inserted into the blade slots in the major cutting guide 62 to perform the desired osteotomies as will be understood by one skilled in the art.

The minor cutting guide may be connected to the support 16 to perform surgeries such as osteotomies. The minor cutting guide 262 is slidably mounted to the support 16 adjacent the distal end 64 of the bone 110 by disposing the shank portion 29 of the rod 18 through the duct 179 and tightening locking bolt 178. The parallel cutting arms 268a and 268b and distal minor cutting guide 270 may be secured in the desired position along the beams 285a and 285b. The drill guides 294a and 294b are secured in position in the drill slots 291a and 291b. Once in position, a surgical blade may be used along inner cutting surfaces 295a and 295b to perform the desired osteotomies. A drill may be used to create fenestrations in the drill holes 293a and 293b in the cutting arms 268a and 268b.

The tibial cutting guide 100 may also be mounted on support 16 to perform surgeries such as osteotomies. The tibial guide member 102 may be mounted to the shank portion 29 of the rod 18. The locking arm 104 is slidably positioned along the tibial guide 102 based on the tibial gauge and locked in position adjacent the proximal end 118 of the tibia 112. The locking arm 104 preferably is placed adjacent to the proximal end 118 of the tibia 112. In this position, the locking arm 104 secures the tibia 112 into a position at an angle to the bone 110. The locking arm 104 may be secured to the proximal end 118 of the tibia 112 with pegs 117 threadably connected to pre-drilled fenestrations (not shown) in the tibia 112.

The tibial template 106 is slidably positioned along the tibial guide member 102 adjacent the proximal end 118 of the tibia 112. The tibial gauge 111 may be used as a reference for determining placement of the tibial template 106. The tibial template 106 may then be locked into the desired position along the tibial guide member 102 with locking bolt 123. Once in position, a surgical blade may be inserted into the tibial blade slots in the tibial template 106 to perform desired osteotomies. Upon completion of the necessary osteotomies, orthopedic knee replacements may be inserted adjacent the distal end 64 of bone 110 and/or the proximal end 118 of tibia 112.

The support 16 may be removed from the patient's bone by reversing the rotational motion of the actuator 50 to axially withdraw the shaft 22 away from the first end 26 of the rod 18. As the shaft 22 moves toward the second end 28 of the rod 18, the roller bearings 20 collapse back through the longitudinal slots 36 and into the collapsed position within the rod 18. In the collapsed position, the roller bearings 20 are retracted as much as necessary to release them from the bone to allow removal of the support 16 from the bone.

Although the invention has been described with respect to a limited number of embodiments, modifications and variations therefrom exist. For example, expandable or non-expandable rods of various lengths and diameters and templates with various blade slots may be used as interchangeable components to allow for further adjustments to meet the patient's needs. The appended claims are intended to cover all such variations and modifications as falling within the scope of invention.

While the present invention has been described by reference to its preferred embodiment, those of ordinary skill in the art will understand that other constructions of surgical instruments for performing orthopedic surgeries are possible which incorporate the disclosed invention. Such other constructions shall be included within the scope of the appended claims.

What is claimed is:

1. An orthopedic surgical system for resection of a distal end of a femur and a proximal end of an adjacent tibia in preparation for implantation of an orthopedic joint replacement, the instrument comprising:
   (a) an intermedullary support comprising an alignment rod having a tapered portion terminating at a first end thereof and defining a longitudinal axis therethrough, the rod axially insertable into the distal medullary cavity of the femur and having an outer surface adapted to engage the femur whereby the rod is alignable within the femur and provides a surgical reference point, the rod having a second end extending a distance beyond the distal femur;
   (b) a cutting guide adjustably mountable to the second end of the rod and positionable about the distal end of the femur, the cutting guide having a plurality of femoral blade slots therethrough, each femoral blade slot adapted to operatively receive a blade whereby the blade is guided to perform osteotomies;
   (c) a tibial guide adjustably mountable to the second end of the rod, non-simultaneously with the cutting guide, and positionable about the proximal end of the tibia, the tibial guide having a plurality of tibial blade slots therethrough, each tibial blade slot adapted to operatively receive a blade whereby the blade is guided to perform osteotomies; and
   (d) a tibial locking arm slidably movable along the tibial guide and adapted to engage the proximal end of the tibia whereby the tibia is secured perpendicular to the femur.

2. The system of claim 1, wherein the tapered portion of the rod defines a plurality of longitudinal slots therethrough positioned radially thereabout, and wherein the support further comprises a plurality of longitudinal roller bearings and a shaft located in the rod, each roller bearing located in one of the longitudinal slots and movable therein between a collapsed position and an expanded position wherein at least a portion of each roller bearing extends beyond the outer surface of the rod in the expanded position, the shaft axially drivable in the rod and adapted to engage the roller bearings, wherein axial advancement of the shaft moves the roller bearings to the expanded position thereby extending the roller bearings into the femur whereby the support is anchored therein in coaxial alignment therewith, and wherein axial retraction of the shaft moves the roller bearings to the collapsed position thereby releasing the roller bearings from the femur whereby the rod is axially removable from the femur.

3. The system of claim 1, wherein the cutting guide comprises a guide member mountable on the support and a posterior template slidably positionable along the guide member, the guide member and the posterior template having some of the femoral blade slots positionable adjacent the distal femur whereby the blade is guided to perform osteotomies.

4. The system of claim 3, wherein the cutting guide further comprises a posterior gauge capable of measuring the position of the posterior template.

5. The system of claim 4, wherein the cutting guide further comprises a distal template slidably positionable along the guide member, the distal template having some of the femoral blade slots positionable adjacent the distal femur whereby the blade is guided to perform osteotomies.

6. The system of claim 5, wherein the cutting guide further comprises a distal gauge capable of measuring the position of the distal template.

7. The system of claim 1, wherein the tibial guide comprises an elongate body member and a tibial template slidably positionable thereon, the body member adjustably mountable to the second end of the rod and positionable about the proximal end of the tibia, the tibial template positionable about the proximal end of the tibia and having some of the tibial blade slots therethrough positionable adjacent the proximal tibia whereby the blade is guided to perform osteotomies.

8. The system of claim 7, wherein the tibial guide further comprises a tibial gauge for measuring the position of the tibial template.

9. The system of claim 1, wherein the cutting guide comprises a mount and a pair of cutting arms, the mount mountable to the support, the mount having a rail adapted to support the cutting arms, the cutting arms slidably positionable along the mount and having cutting surfaces positionable adjacent the distal femur whereby the blade is guided to perform osteotomies.

10. The system of claim 9, wherein the cutting guide further comprises a second rail and a cutting block, the second rail positionable parallel to the first rail, the cutting arms slidably positionable along the first and second rails, the cutting block slidably positionable along the second rail between the cutting arms, the cutting block having at least one femoral blade slots therethrough positionable adjacent the distal femur whereby the blade is guided to perform osteotomies.

11. A surgical system for orthopedic resection of a bone, comprising:
   (a) an intermedullary support comprising an alignment rod, a plurality of longitudinal roller bearings, and an internal shaft therein, the alignment rod defining a longitudinal axis and having a tapered portion terminating at a first end thereof coaxially insertable into the medullary cavity of the bone and a second end extending beyond the bone, the tapered portion having an outer surface adapted to engage the bone and defining a plurality of longitudinal roller bearing slots therethrough positioned radially thereabout, each roller bearing located in one of the longitudinal roller bearing slots and movable therein between a collapsed position and an expanded position, the internal shaft axially movable within the rod and adapted to engage the roller bearings, wherein at least a portion of each roller bearing extends a distance beyond the outer surface of the rod in the expanded position, wherein axial advancement of the shaft moves the roller bearings to the expanded position thereby extending the roller bearings into the bone so that the support is anchored therein in coaxial alignment therewith whereby the rod provides a surgical reference point; and (b) a cutting guide adjustably mountable to the second end of the rod and positionable about an end of the bone, the cutting guide having a plurality of blade slots therethrough, each blade slot adapted to operatively receive a blade whereby the blade is guided to perform osteotomies.

12. The system of claim 11, wherein the cutting guide comprises a cutting guide member and a posterior template, the cutting guide member mountable to the support, the posterior template slidably positionable along the cutting guide member, the posterior template having some of the blade slots therethrough positionable adjacent the bone whereby the blade is guided to perform osteotomies.

13. The system of claim 12, wherein the cutting guide further comprises a posterior gauge capable of measuring the position of the posterior template.

14. The system of claim 13, wherein the cutting guide further comprises a distal template slidably positionable along the cutting guide member, the distal template having some of the blade slots therethrough positionable adjacent the bone whereby the blade is guided to perform osteotomies.

15. The system of claim 14, wherein the cutting guide further comprises a distal gauge capable of measuring the position of the distal template.

16. The system of claim 15, wherein the bone is a femur adjacent a tibia, wherein the instrument further comprises a tibial guide mountable to the support, non-simultaneously with the cutting guide, the tibial guide having a plurality of tibial blade slots therethrough adapted to positionably receive a blade whereby the blade is guided to perform osteotomies.

17. The system of claim 16, further comprising an elongate body member and a tibial locking arm slidably movable along the body member and adapted to engage the proximal end of the tibia whereby the tibia is secured perpendicular to the femur.

18. The system of claim 17, wherein the tibial guide comprises a tibial template slidably positionable along the body member, the tibial template having tibial blade slots therethrough positionable about the proximal tibia whereby the blade is guided to perform osteotomies.

19. The system of claim 18, wherein the tibial guide further comprises a tibial gauge for measuring the position of the tibial template.

20. The system of claim 11, wherein the cutting guide comprises a mount and a pair of cutting arms, the mount mountable on the support, the cutting arms slidably positionable along the mount, the cutting arms having cutting surfaces positionable adjacent the bone whereby the blade is guided to perform osteotomies.

21. The system of claim 20, wherein the cutting guide further comprises a cutting block slidably positionable along the mount, the cutting block having a blade slot therethrough positionable adjacent the bone whereby the blade is guided to perform osteotomies.

* * * * *